United States Patent
Emokpae (10) Patent No.: US 11,445,909 B2
(45) Date of Patent: Sep. 20, 2022

(54) BODY AREA SENSOR NETWORK BIO-FEEDBACK SYSTEM

(71) Applicant: Lasarrus Clinic and Research Center, LLC, Baltimore, MD (US)

(72) Inventor: Lloyd Erhunwunse Emokpae, Glen Burnie, MD (US)

(73) Assignee: Lasarrus Clinic and Research Center, LLC, Baltimore, MD (US)

(*) Notice: Subject to any disclaimer, the term of this patent is extended or adjusted under 35 U.S.C. 154(b) by 214 days.

(21) Appl. No.: 16/861,824

(22) Filed: Apr. 29, 2020

(65) Prior Publication Data

US 2021/0169326 A1 Jun. 10, 2021

Related U.S. Application Data

(60) Provisional application No. 62/944,348, filed on Dec. 5, 2019.

(51) Int. Cl.
| | |
|---|---|
| *A61B 5/00* | (2006.01) |
| *H04W 4/38* | (2018.01) |
| *A61B 5/0205* | (2006.01) |
| *A41D 1/00* | (2018.01) |
| *H04L 67/12* | (2022.01) |
| *A63B 24/00* | (2006.01) |
| *H04W 84/20* | (2009.01) |
| *G16Y 20/40* | (2020.01) |

(Continued)

(52) U.S. Cl.
CPC ............ *A61B 5/0024* (2013.01); *A41D 1/002* (2013.01); *A61B 5/0205* (2013.01); *A61B 5/6804* (2013.01); *H04L 67/12* (2013.01); *H04W 4/38* (2018.02); *A61B 5/332* (2021.01); *A61B 5/389* (2021.01); *A61B 7/04* (2013.01); *A61B 8/4209* (2013.01); *A61B 2562/0219* (2013.01); *A63B 24/0062* (2013.01); *G16Y 20/40* (2020.01); *G16Y 40/20* (2020.01); *H04W 84/20* (2013.01)

(58) Field of Classification Search
None
See application file for complete search history.

(56) References Cited

U.S. PATENT DOCUMENTS

| | | | |
|---|---|---|---|
| 8,340,740 | B2 | 12/2012 | Holzer et al. |
| 9,582,072 | B2 | 2/2017 | Connor |

(Continued)

FOREIGN PATENT DOCUMENTS

| | | | | |
|---|---|---|---|---|
| WO | WO-2017190049 A1 | * | 11/2017 | ............. A43B 17/00 |
| WO | WO-2018136462 A1 | * | 7/2018 | ........... A61B 5/0017 |

OTHER PUBLICATIONS

Ted Kritsonis, Hands-on: Clipless, https://www.digitaltrends.com/mobile/hands-clipless/, Nov. 24, 2014, viewed on Jan. 25, 2022.*

*Primary Examiner* — Lynsey C Eiseman
*Assistant Examiner* — James Moss
(74) *Attorney, Agent, or Firm* — U. Maryland Baltimore Carey School of Law MIPLRC/IPEC (57) ABSTRACT

This system is a network of sensor nodes with multiple sensors at each node. The nodes are used in combination with a wearable garment to enable multiple types of data to be combined together to produce a fuller picture of a body's physiological state; such as during physical therapy. In addition, the system utilizes acoustic imaging to measure muscle activation. The system transmit this data to a host computer to visualize various data comparisons.

11 Claims, 14 Drawing Sheets

(51) Int. Cl.
  *G16Y 40/20*      (2020.01)
  *A61B 7/04*       (2006.01)
  *A61B 8/00*       (2006.01)
  *A61B 5/332*      (2021.01)
  *A61B 5/389*      (2021.01)

(56) References Cited

U.S. PATENT DOCUMENTS

| | | | |
|---|---|---|---|
| 10,456,604 B2 | 10/2019 | Cheatham, III et al. | |
| 2015/0309563 A1 | 10/2015 | Connor | |
| 2015/0351690 A1* | 12/2015 | Toth | A61B 5/14517 |
| | | | 600/391 |
| 2017/0143977 A1 | 5/2017 | Kaib et al. | |
| 2017/0157430 A1 | 6/2017 | Cheatham, III et al. | |
| 2018/0139518 A1* | 5/2018 | Touma | A63B 43/00 |
| 2019/0134396 A1* | 5/2019 | Toth | A61N 1/36003 |
| 2019/0231262 A1* | 8/2019 | Nasry | A61B 7/026 |
| 2019/0298987 A1 | 10/2019 | Freeman et al. | |
| 2019/0365263 A1* | 12/2019 | Raj | A61B 5/6833 |

* cited by examiner

BODY AREA SENSOR NETWORK BIO-FEEDBACK SYSTEM

CROSS-REFERENCE TO RELATED APPLICATIONS

This application claims priority to U.S. Provisional Application Ser. No. 62/944,348, filed Dec. 5, 2019, the disclosure of which is incorporated by reference in its entirety.

BACKGROUND

Over 800,000 people per year suffer from strokes, making it the leading cause of permanent disability in the country. The human brain is capable of self-reorganizing, known as neuroplasticity. The brain can reestablish the neural pathways that control movement, especially after limb stimulation is employed. Moreover, providing instantaneous feedback during the rehabilitation process can speed up recovery. The ability to regain functionality of the upper extremity is one of the main goals of physical therapy. Upper extremity use is critical for performing activities of daily living such as writing, eating, and walking.

Current forms of physical therapy do not provide patients with a high level of quantitative measurement of progress. The patient may face motivational challenges without any quantitative data to measure progress when improvements are subtle and gradual. Further, short term goals are difficult to set and reach without quantitative data. Some devices can measure single points of data, but none provide a holistic view of the patient's progress.

DETAILED DESCRIPTION

The present invention will be described in preferred embodiments. The invention may, however, be embodied in many different forms and should not be construed as being limited to the embodiments set forth herein; rather, these embodiments are provided so that this disclosure will be thorough and complete, and will fully convey the concept of the invention to those skilled in the art.

The present invention may provide patients with instantaneous audible and visual feedback regarding progress being made during physical therapy. In addition, the invention may provide the patient with aggregated data from multiple sensor types at multiple locations on his body over the long term of his rehabilitation. This type of data may help a physical or occupational therapist measure and track a patient's progress and provide encouragement to the patient.

Smart Shirt

Figure 1:
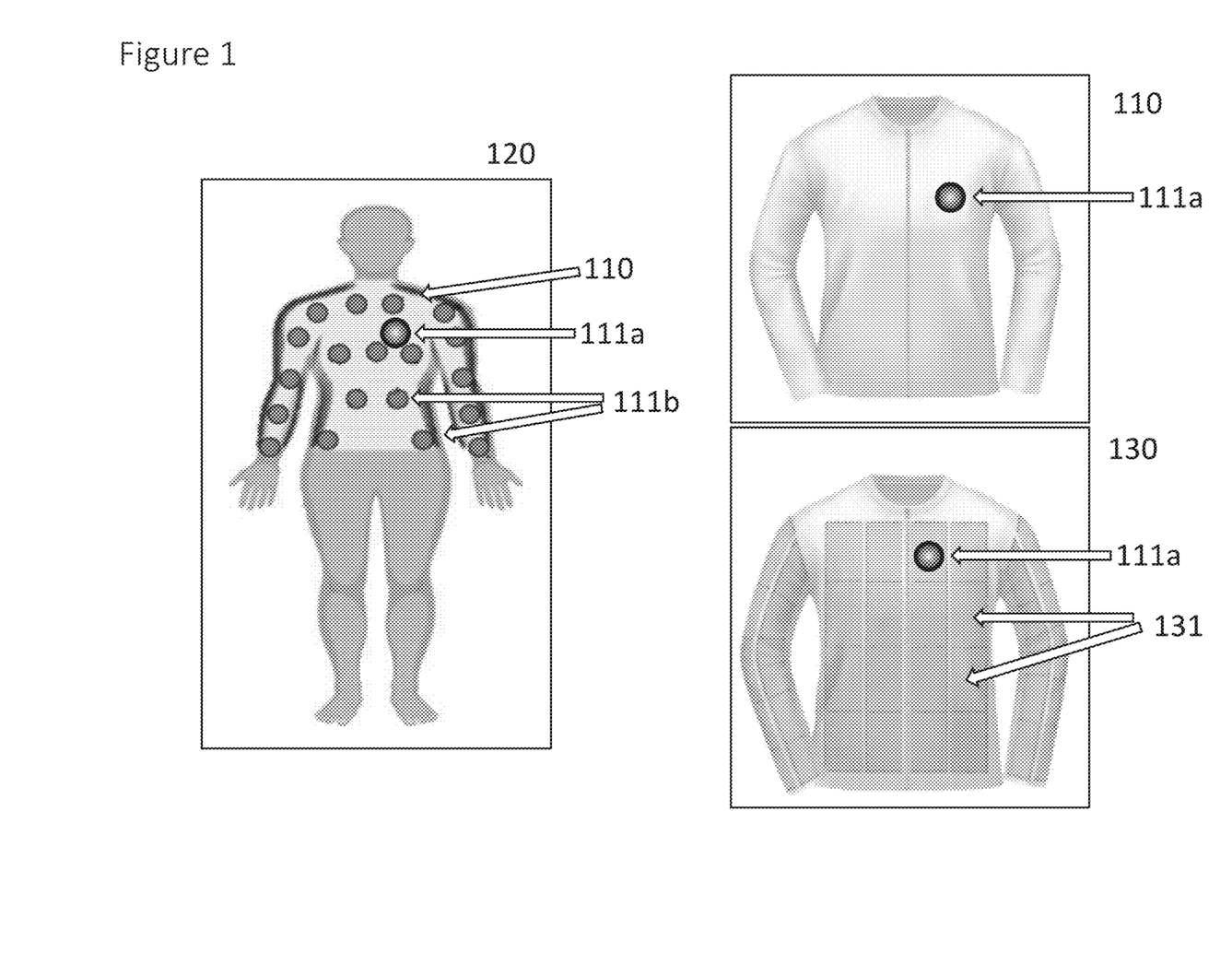
FIG. 1 illustrates two embodiments of the invention, including a wearable garment, a master node, and a plurality of slave nodes.

In an embodiment depicted in FIG. 1, the invention may be a system that consists of (1) a wearable article of clothing (such as a short- or long-sleeved shirt) 110 with integrated wireless sensor nodes 111 to measure the physiological and biokinetic states of a user, and a (2) an integrated processor for sensor fusion and machine learning, where a master node 111a processes the data gathered from the sensor nodes 111. An alternate view of the shirt 130 depicts a plurality of pockets 131 integrated into the shirt. The pockets 131 are where a user of the shirt can insert up to 20 respective nodes 111 including the master node 111a and up to 19 slave nodes 111b.

Figure 2:
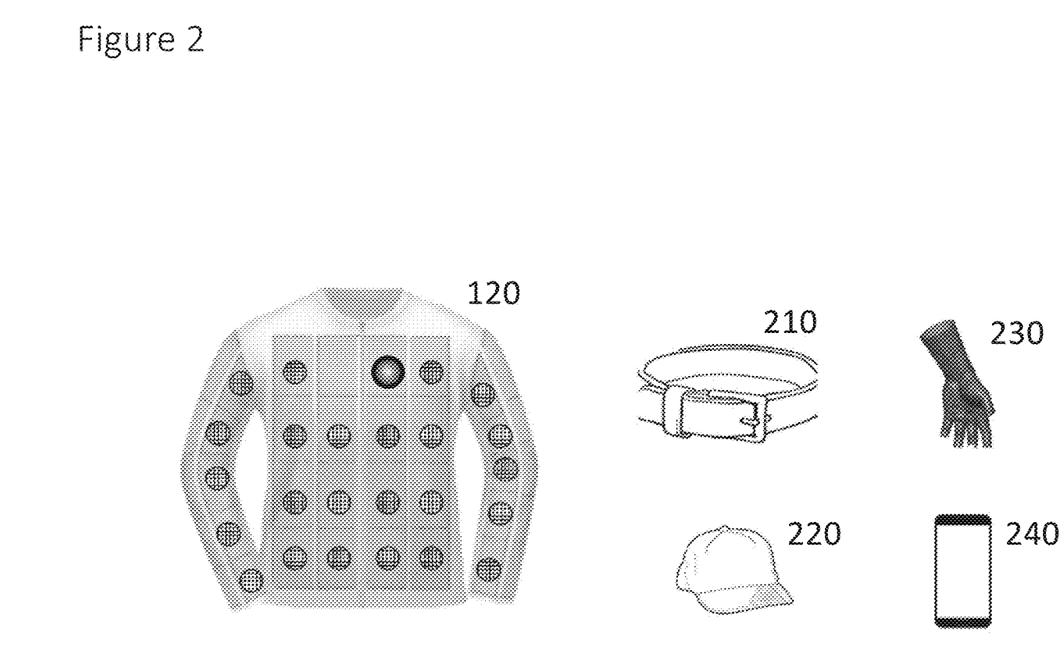
FIG. 2 demonstrates several embodiments of the master node of the invention.

Various embodiments of the invention 120 are depicted in FIG. 2. A pocket for the master node 111a may be sewn into, or otherwise attached to, a belt 210, a glove 220, or a head covering 230. The master node 111a may also be embodied in a smart phone device 240 in conjunction with an app. The master node 111a may be placed anywhere such that it can be closely connected to the slave node(s) 111b.

Nodes Generally

Figure 3:
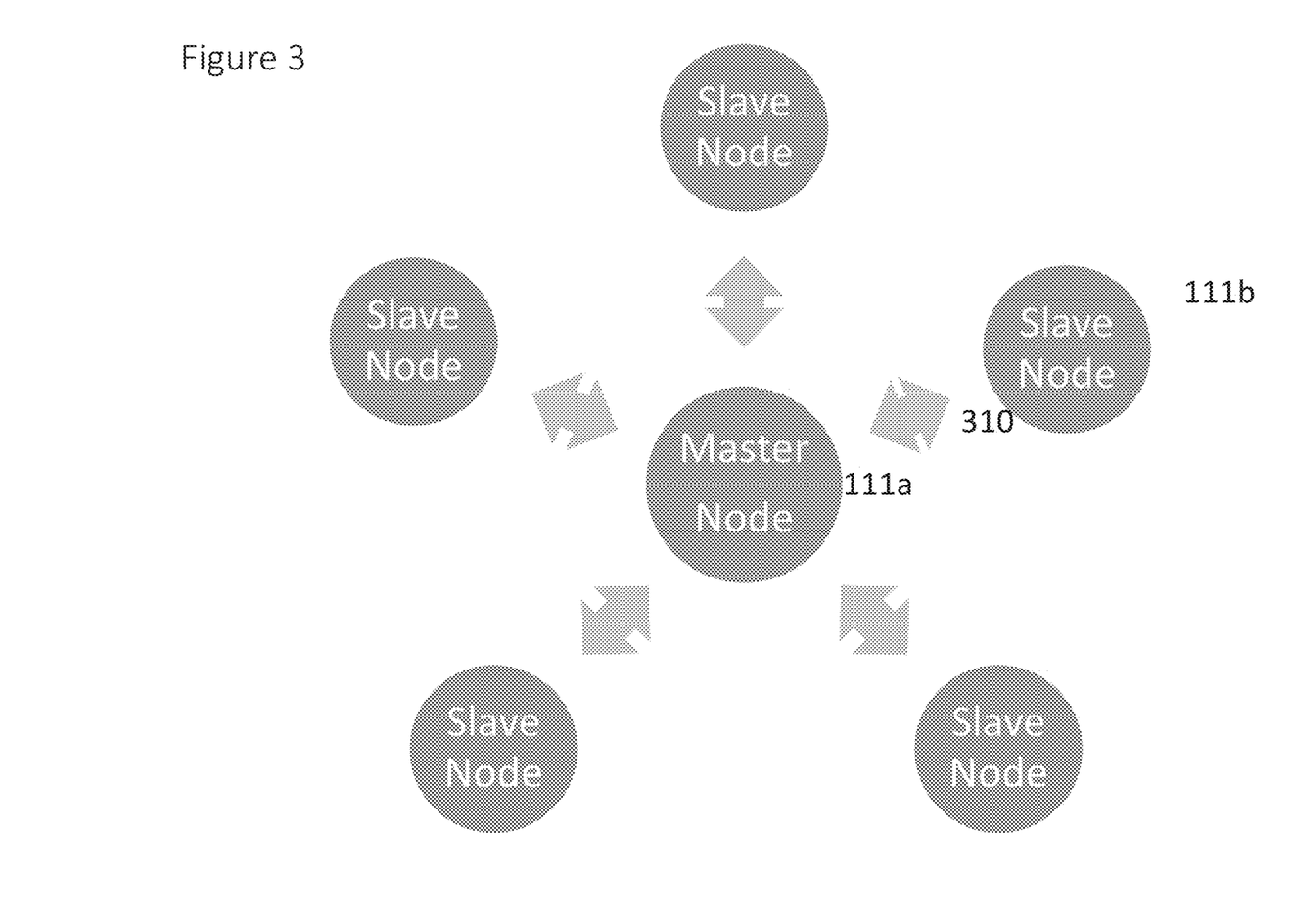
FIG. 3 visualizes the wireless interconnectivity between the master node and the slave nodes of an embodiment.

FIG. 3 depicts the connectivity between the master node 111a and the slave node(s) 111b. The master node 111a may communicate with the slave nodes wirelessly 310. For example, the master node 111a may communicate through ZigBee and/or Bluetooth. Alternatively, some or all of the connections between master node 111a and the respective slave nodes may be wired.

Furthermore, this invention includes a distributed processing system with a master node 111a and multiple slave nodes.

Each node 111 node incorporates multimodal sensors, including, but not limited to, electrical, micro-electro-mechanical systems (MEMS), and acoustics for measuring both torso range of motion and the physiological state of a user at a specific integration point such as (but not limited to) the user's shoulder, biceps, chest, or back.

The nodes 111 in this system use acoustic sensors different from the prior art. The acoustic sensors noninvasively and wirelessly measure muscle activation and perform imaging of muscle tissue and/or large body organs. For example, the acoustic sensors measure muscle activation of the user's heart or lungs. The node 111 does not require close contact to the human body, unlike what is normally required for electrical cardiography (ECG) sensing.

Master Node

Figure 4:
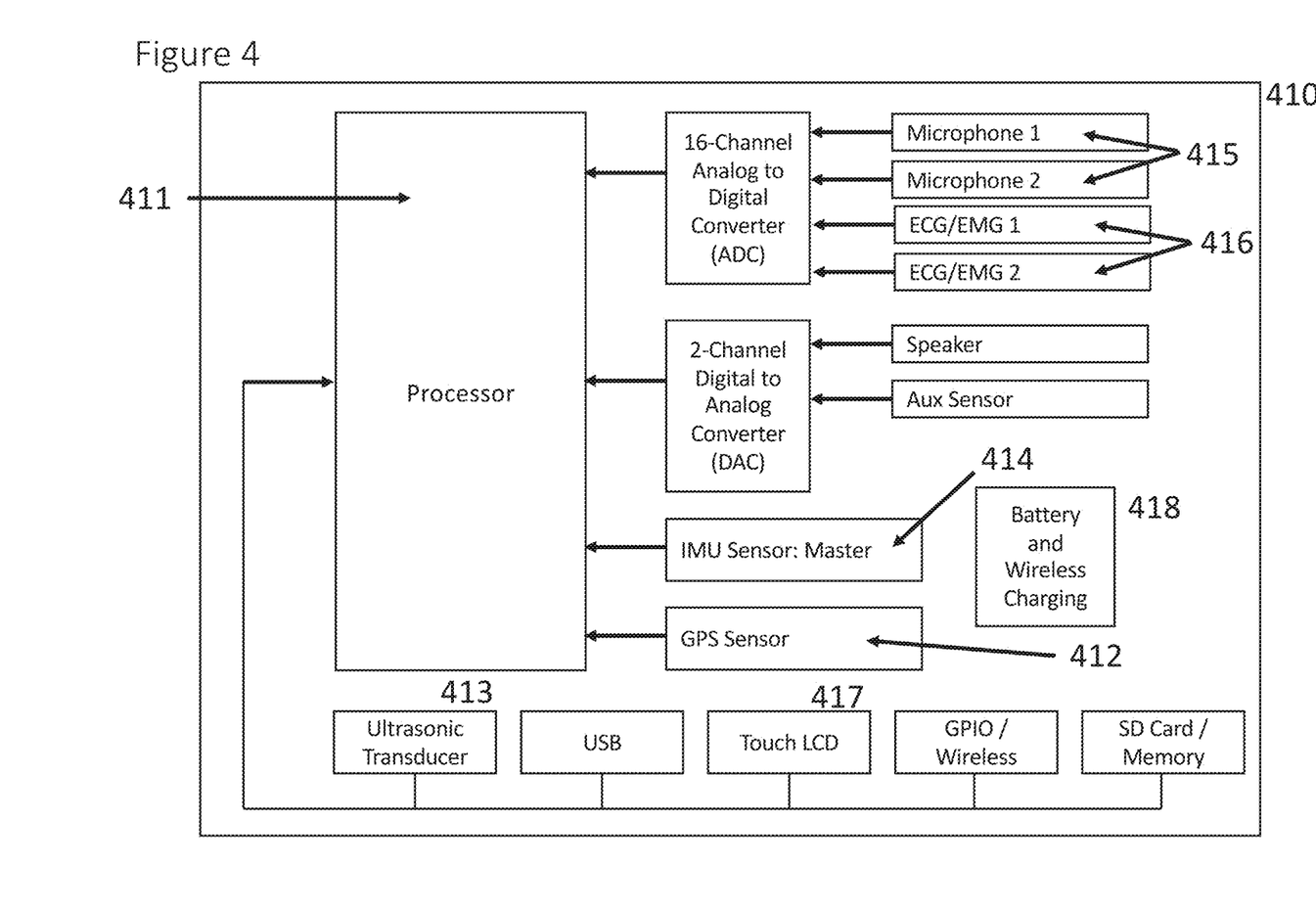
FIG. 4 illustrates a circuit diagram of the master node, in an embodiment.

FIG. 4 depicts a high-level diagram 410 of the master node 111a. Each master node contains a high-fidelity processor 411, for example, a Service on Chip (SoC) field programmable gate array (FPGA), to perform: data fusion of the received data from all slave nodes, incorporating one or more machine learning algorithms that learn and track exercises of the user, incorporating algorithms for performing imaging of the human body from the recorded acoustic data streams, and/or interfacing to a virtual reality (VR) game for sensor biofeedback. The master node 111a may incorporate a high-fidelity processor 411 for real-time data processing. This processing may include wireless clock synchronization, wireless beamforming, sensor fusion and/or machine learning. The processor 411 functions are further described in paragraph 0046-0050.

The master node may incorporate a GPS sensor 412 as a reference input for network clock synchronization.

The master node 111a may include multiple sensors for enabling bio-feedback: including, for example, an ultrasonic transducer 413 to provide a sound source for organ imaging; a MEMS inertial management unit (IMU) 414 for range-of-motion sensing; two acoustic microphones 415 to be used for imaging, acoustic cardiography (ACG), and acoustic myography (AMG), and electrical sensors 416 for ECG and electrical myography (EMG). The master node 111a may also incorporate a touchscreen liquid crystal display 417 for interfacing with the software functions on the node.

Slave Nodes

Figure 5:
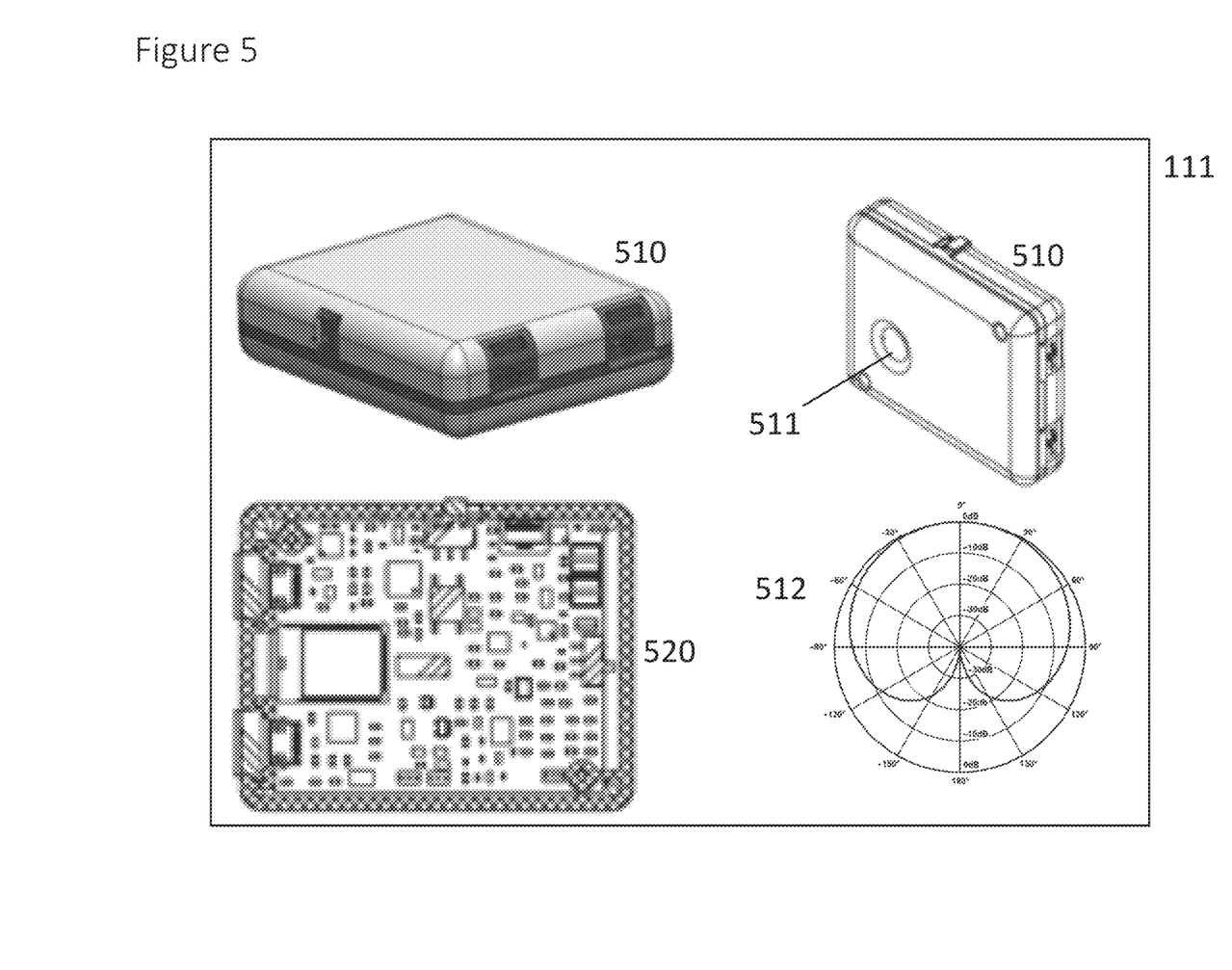
FIG. 5 demonstrates an embodiment of the node housing.

In the embodiment of FIG. 5, the slave nodes have an outer housing 510 and an internal circuit board 520. The housing 510 has strategic openings 511 to facilitate sensor readings. The cardioid acoustic beam pattern 512 from combining the 2-element microphone on each slave node has no signal attenuation to the front of an array, but complete signal isolation/cancellation on the sound incident to the array at 180°.

Figure 6:
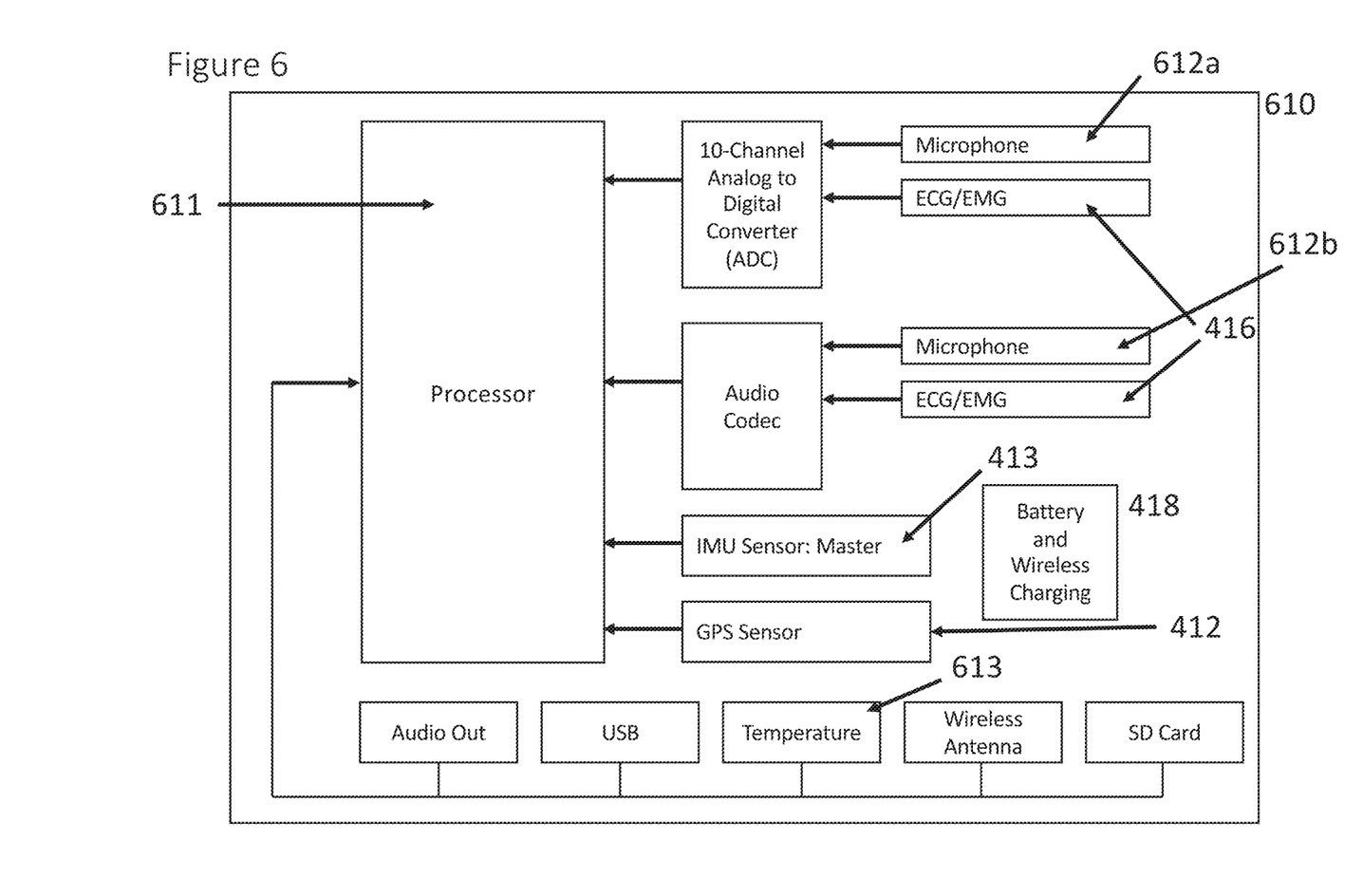
FIG. 6 illustrates a circuit diagram of the slave node, in an embodiment.

FIG. 6 depicts a high-level diagram 610 of the slave node 111b according to an embodiment. Each slave node 111b contains a low-fidelity processor 611. The processor 611 may perform: time synchronization for data fusion; processing localized inertial range of motion at the sensor location; processing localized acoustic; electrical sensor data for acoustic, ECG, and/or Cardiography; and/or transmitting processed localized data to the master node.

The slave nodes 111b may be inserted in respective pockets 131 strategically located throughout the shirt. Some nodes 111b may be placed around joints, the chest, and back for example and without limitation. The slave nodes 111b may be placed in these areas to noninvasively measure muscle activation and perform imaging of muscle tissues and large body organs. The slave nodes 111b may include a MEMS IMU 414 for range of motion at the joint, acoustic sensing with ACG and AMG, and electrical sensing with ECG and EMG.

The two microphones 612 on the slave nodes 111b may provide two different functions. One microphone 612a may be positioned outward to listen for ambient sounds. The other microphone 612b may be positioned inward. The inward-facing microphone 612b may utilize a built-in mechanical funnel 511 to listen to sounds close to the user's body. The data from the outward-facing microphone 612a may assist the system to differentiate outside noises heard on the inward-facing microphone 612b through active noise cancelation.

Figure 7:
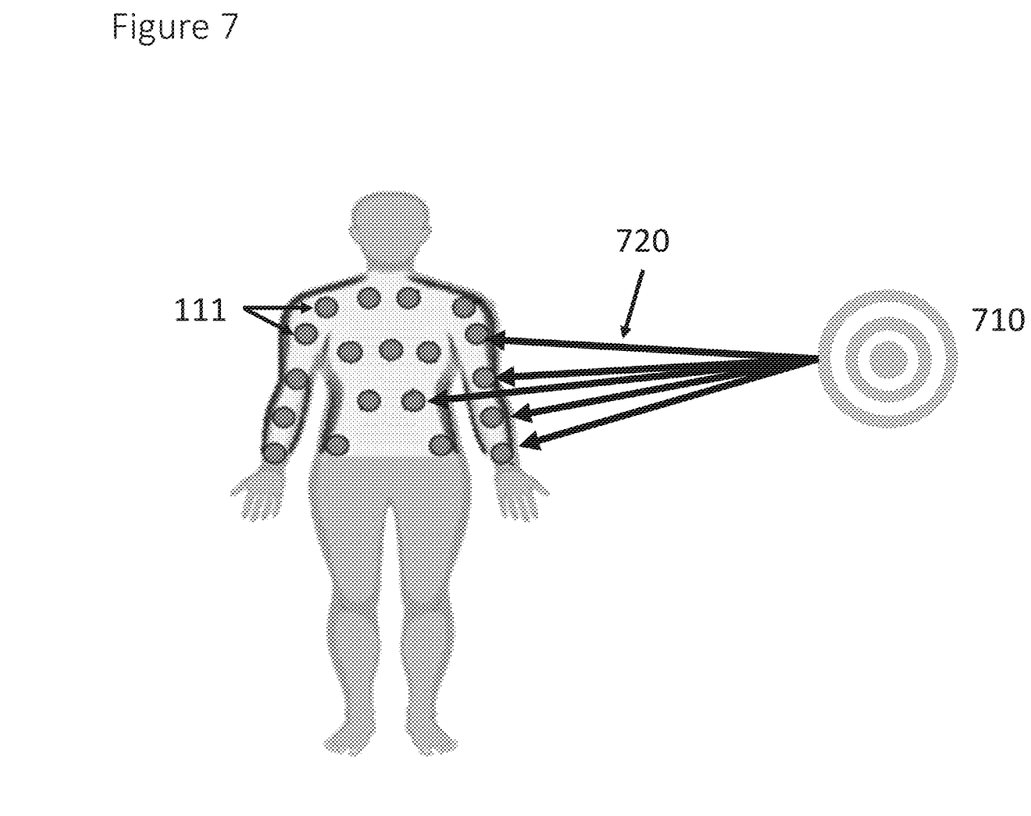
FIG. 7 demonstrates multilateration of any external acoustic signal, in an embodiment.

In an embodiment shown in FIG. 7, the system may estimate the position of external sounds 710 near the user. One method of estimating the noise location may involve multilateration. Multilateration, also called hyperbolic positioning, is the process of locating an object by the precise calculation of the time difference of arrival (TDOA) of the signal to different base stations. The clocks on the nodes 111 must be precisely synchronized to enable multilateration. In addition, the nodes must be able to detect their relative distance from each other.

The system 120 may perform multilateration by recording the precise time that the node 111 detected the external acoustic source 710. The system may use the TDOA between each node 111b to determine the location of the external acoustic source 710 using any of several algorithms that are well known in the field of multilateration. For example, a person knowledgeable in the field may select to use a Taylor Series least-squares algorithm to calculate the position of the external acoustic source 710 after finding the TDOA. Other methods of calculation well known in the field include the Chan, Fang, SI, and SX methods.

One potential application of estimating the position of the acoustic source 710 may be for law enforcement. A police officer may be informed of the position of ballistic sounds to locate the source 710 more quickly, especially in the case of an active-shooter.

Figure 8:
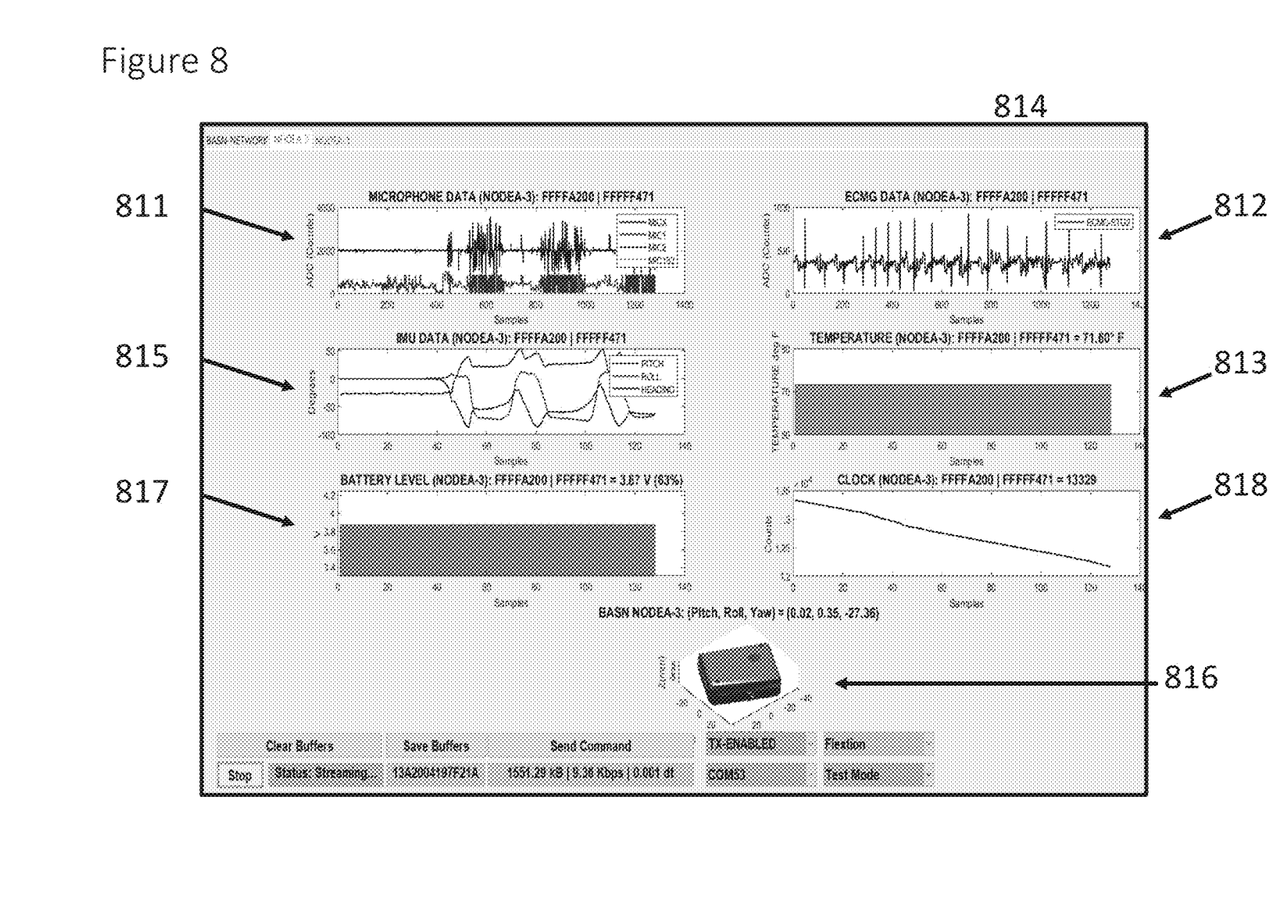
FIG. 8 demonstrates an embodiment of a node information display screen.

In another embodiment, the device performs lung and heart auscultation using nodes 111 placed at multiple locations on the user's chest and the sensor data from the microphones 612 and the ECG/EMG 416. A medical professional may interpret the results based on a visual representation of the sensor data, such as depicted in FIG. 8. The medical professional would read and interpret the acoustic cardiography 811 and the ECG/EMG Sinus Heart Pattern 812 based on the medical professional's experience.

In another embodiment, the device performs cardiac acoustic mapping using the sensor data from the microphones 612 and the ECG/EMG 416. The nodes 111 may be placed in known locations around the chest such as how the nodes 111 are placed in FIG. 9. In this instance, "known" means that the sensor locations are defined within the accompanying software. A medical professional interprets the data represented in a display such as FIG. 8 to detect diseases such as cardiovascular disease.

Figure 9:
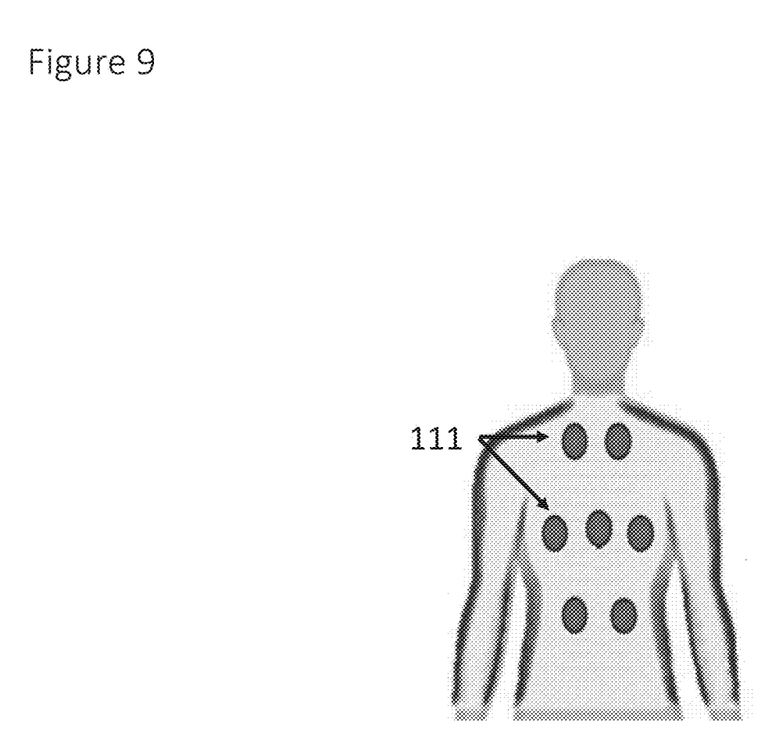
FIG. 9 demonstrates node placement for an embodiment of cardiac and respiratory monitoring.

Another embodiment of the device detects lung inflammation and fever conditions when the nodes 111 are placed on the user's chest such as depicted in FIG. 9. A medical professional can interpret the data on a display such as FIG. 8 to remotely diagnose symptoms of upper respiratory tract infection. The medical professional may view the patient's temperature on the temperature chart 813 and the lung sounds on the acoustic measurement chart 811.

Node Identification

Figure 10:
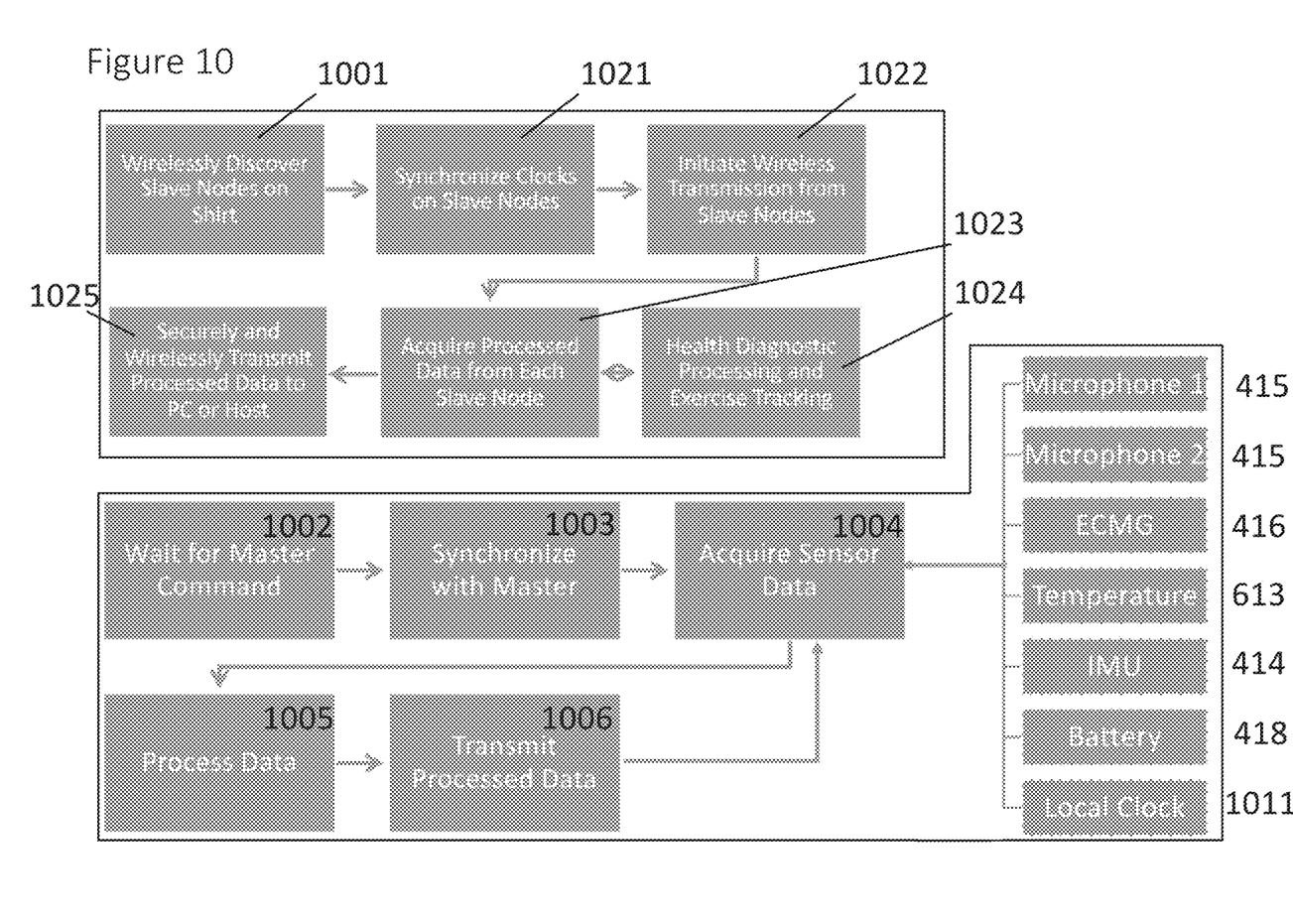
FIG. 10 demonstrates the process of the slave node sensing and the master node receiving and processing the slave node sensor data, in an embodiment.

In an embodiment shown in FIG. 10, the master node 111a contains software for a discovery mode. An embodiment of the discovery mode is where the master node 111a continuously attempts to discover 1001 any active slave nodes 111b. In another embodiment, the master node 111a only attempts to discover 1001 active nodes 111b within a specified period of time after the master node 111a is activated. In another embodiment, the master node 111a only attempts to discover 1001 active nodes 111b when the user activates a discovery mode. The master node 111a identifies each slave node 111b with a unique identification number when the master 111a discovers 1001 the slave nodes 111b.

Figure 11:
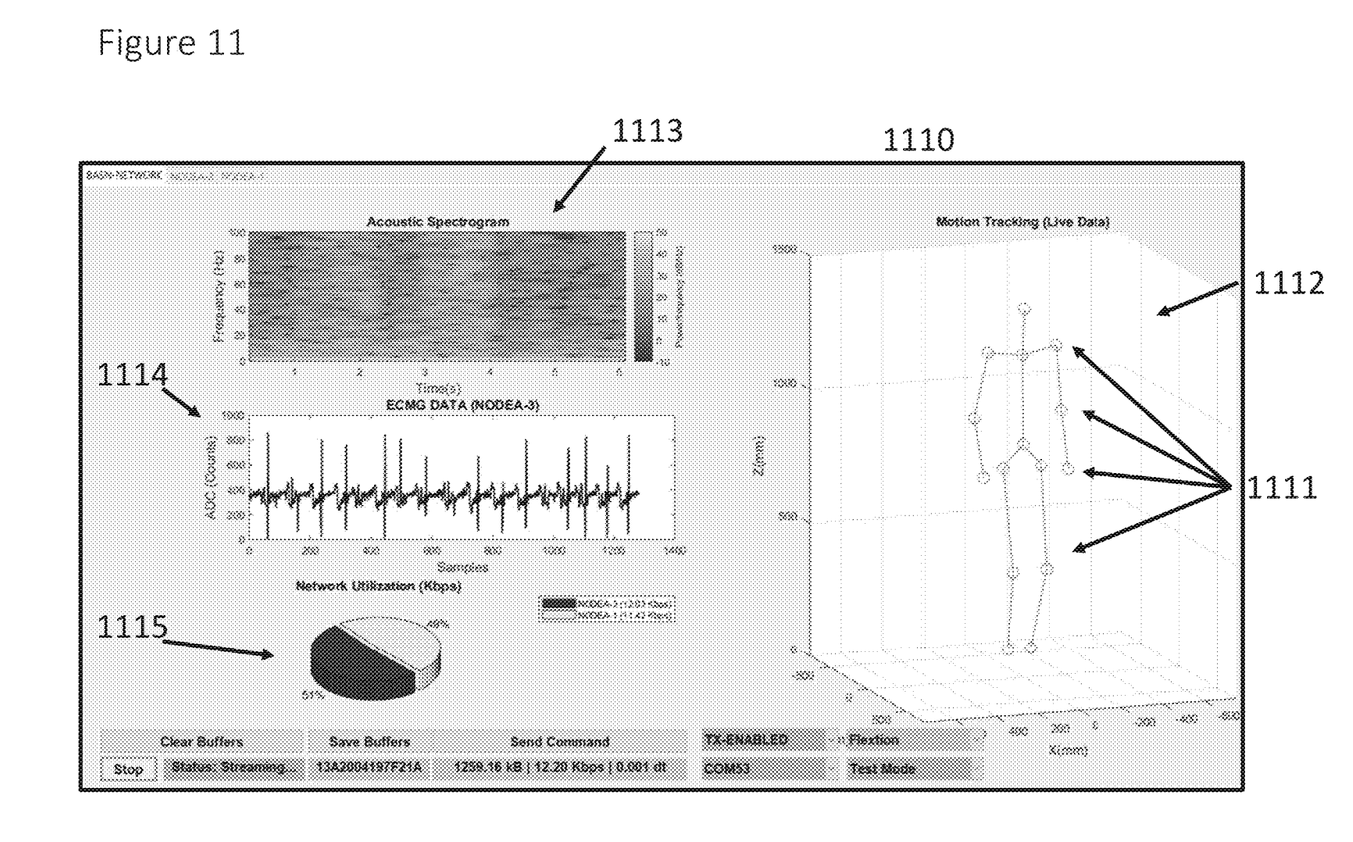
FIG. 11 demonstrates a second embodiment of a node information display screen.

FIG. 11 depicts a screenshot of one embodiment of a node information display 1110 within an accompanying software package. Each node 111 may be displayed on a separate display page 1110 in the accompanying software. The user may then assign each node 111 to a location 1111 on a human model 1112 when the master node discovers 1001 a new node 111b.

Body Sensor Network Bio-Feedback System

Returning to FIG. 10, this depicts the process flows for the sensor network and the slave nodes.

After the user activates the slave node 111b, the slave node 111b waits for the master node 111a to send a command 1002. When the slave node 111b receives a command from the master node 111, the slave node 111b and the master node 111a synchronize clocks 1003. The slave node 111b then acquires data from the various onboard sensors 1004. For example, these sensors include two microphones 612, an ECG/EMG 415, a thermometer 613, an IMU 413, the battery 418, and the local clock 1011. The slave node 111b processes the data locally 1005 then transmits the processed data to the master node 111a for further processing 1006. The slave node 111b returns to the data acquisition step 1004 and repeats this process (1004-1006) until the slave node 111b receives a new command from the master node 111a or the user turns off slave node 111b.

The user may select where and what he wants to measure and place slave nodes 111b in the appropriate areas to make the desired measurements. The user may select which body part the user wants to measure. These measurements may include, but are not limited to, joint sounds, muscle activation, heart sounds, pulse, range of motion, electrocardiography, and/or muscle imaging. First, the master 111a and slave nodes 111b are activated by the user. Then, the master node 111a wirelessly discovers the slave nodes 111b that are currently active 1001. During this step, the master node 111a identifies each slave node 111b. The master node 111a tracks the slave nodes' 111b unique identification numbers throughout the remaining steps. The master node 111a synchronizes the clocks 1021 on all the nodes 111. Synchronization may be achieved by a beacon message from the master node 111a to the slave nodes 111b. Then, the master node 111a initiates wireless transmission 1022 by sending a command to each slave node 111b. The master node 111a acquires data 1023 from each slave node 111b. Then, the master node processor 411 may perform health diagnostics and tracks exercises 1024. Finally, the master node 111a may store the data locally or wirelessly and securely transmit processed data to a PC or other host 1025.

In an embodiment, the system utilizes biometric feedback data acquired in the process in paragraph 0048 to identify the user. Further, the system may use the user identification step to prevent anyone but the authorized user from accessing and/or transmitting the user's data.

Node Information Display

In the embodiment of FIG. 11, the node display page 1110 may depict the human model 1112 with the node's 111 relative position to the other nodes 111, a real-time acoustic spectrogram 1113, a real-time ECG/EMG graph 1114, and/or the node's 111 wireless network utilization 1115. The spectrogram 1113 may display the node's 111 received acoustic signal over time. The network utilization 1115 helps the user to troubleshoot a problem with the wireless network. The process described in paragraphs 0046-0050 may be utilized to update the data received by the accompanying software package.

When the system wearer moves his body, the display page 1110 may update the human model 1112 to reflect the node's 111 changed relative spatial location. The data from the IMU sensor 413 and GPS 412 may be used to calculate the node's 111 changing relative spatial location.

FIG. 8 depicts a second embodiment of an individual node display screen 814. This display screen 814 may display the acoustic data 811 from the microphones (415, 612), the IMU data (pitch, roll and yaw) in both a graph over time 815 and a display of the IMU's 414 current orientation 816, the node's battery level 817, a real-time ECG/EMG graph 812, temperature over time 813, and real-time clock information 818.

The acoustic display 811 may also display the noise-cancelled acoustic waveform. This waveform may be calculated by subtracting the outer microphone 612a is from the inner microphone 612b.

A specialist may be able to infer information from the node display pages 814. For instance, on the temperature display 813, a 2-degree difference between a node on the user's elbow versus the user's arm may indicate the amount of blood flow being used to perform a movement. The IMU display 815 may indicate the user's range of motion during a movement at a joint where the node 111 was placed.

Figure 12:
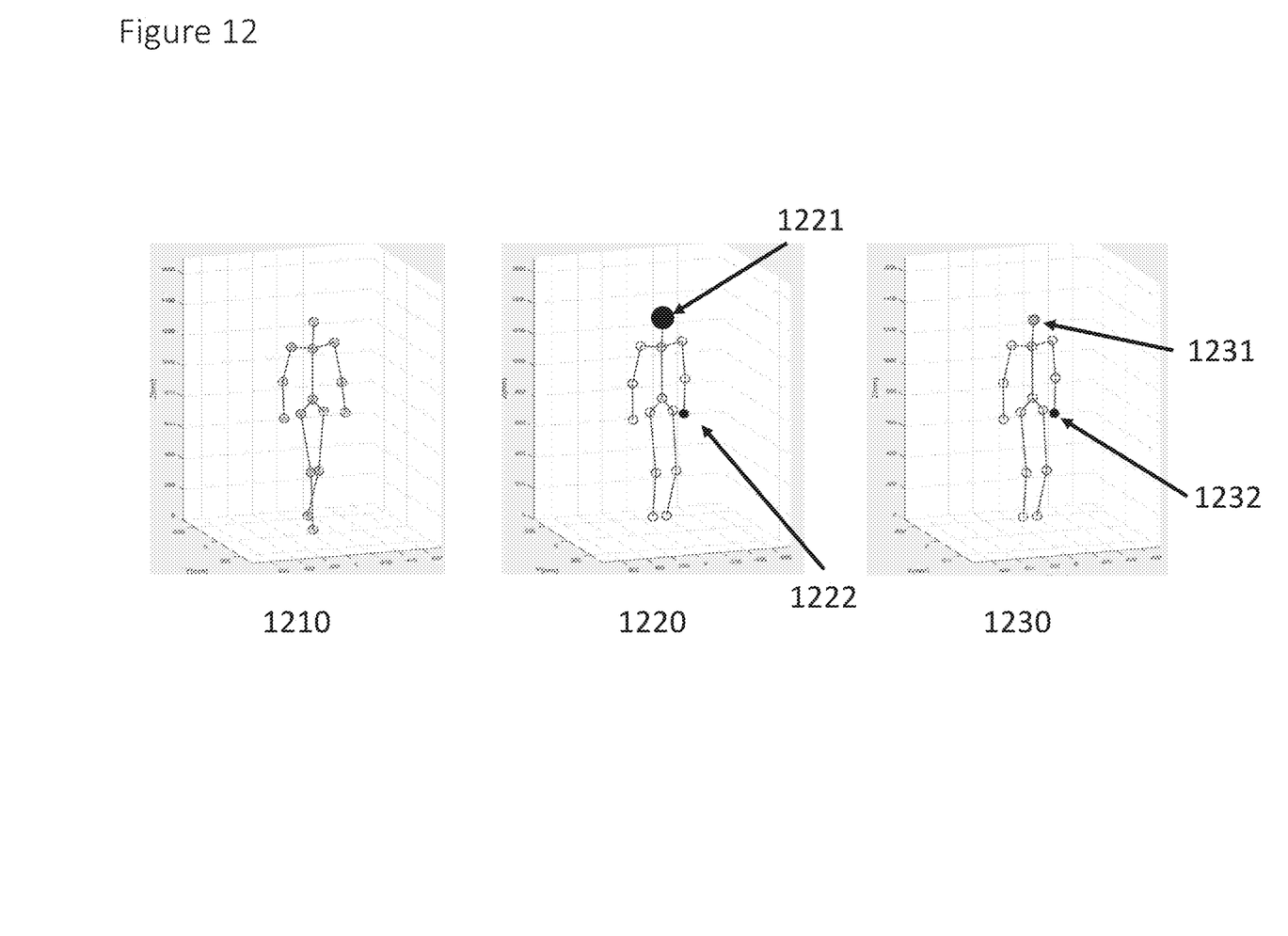
FIG. 12 demonstrates three embodiments of a node information display screen.

FIG. 12 depicts an embodiment of a display screen with a skeletal model where the user can select different data overlays. The three representations of this embodiment are shown, but any combination of the available data may be displayed. The first overlay 1210 depicts the battery level of each node 111. The color of each node 111 shifts from green to red as the battery level decreases. The second overlay 1220 depicts an acoustic overlay of sounds around the body. The size of the node 111 increases as an acoustic source nears the node 111. A user may infer that a noise source is near the head because one node 1221 in this overlay 1220 is much larger than the other active node 1222. The third overlay 1230 is for temperature. A warmer color 1231 represents a warmer temperature than the other active node 1232.

Physical Therapy and VR Integration

In an embodiment, the system provides biofeedback to a physical/occupational therapist while a patient performs a series of exercises. The combination of the master node 111a, the slave node(s) 111b, and the wearable shirt 110 may be used as a real-time bio-feedback tool to assist a physical or occupational therapist and his patient during physical therapy.

Figure 13:
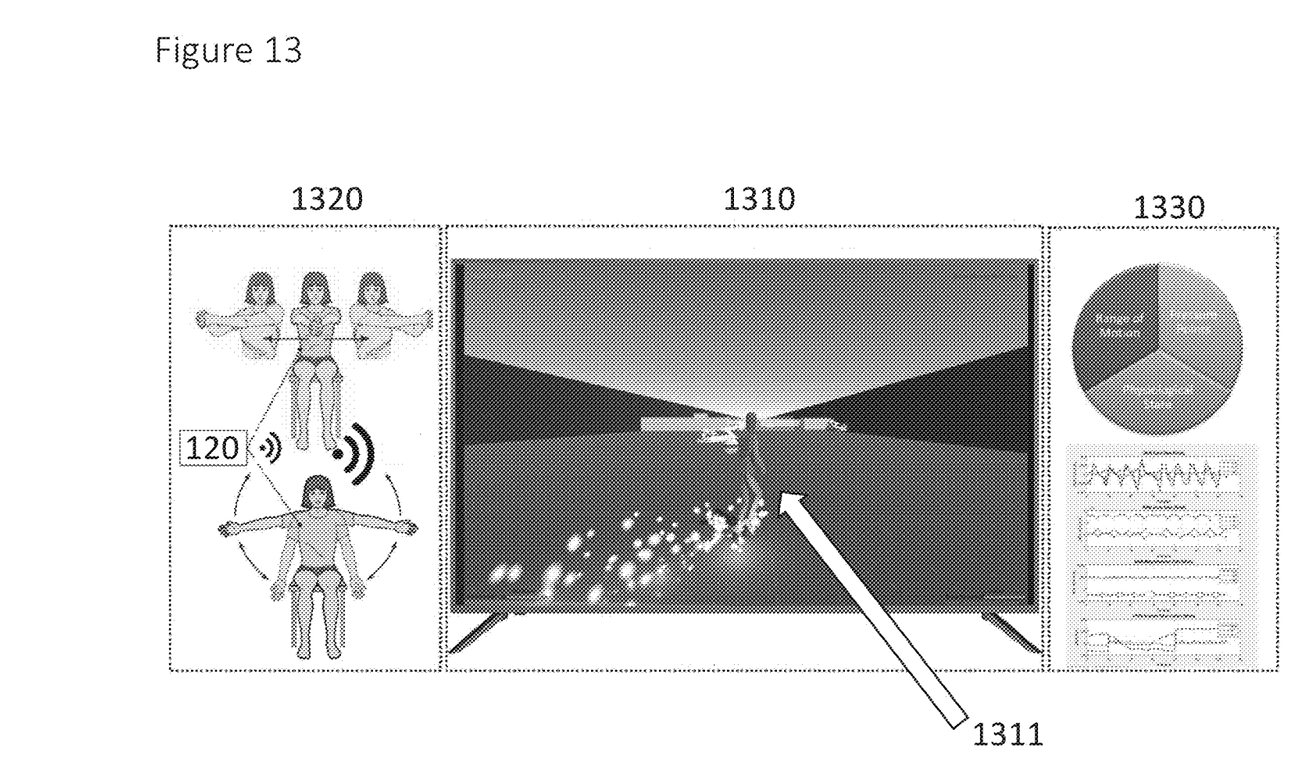
FIG. 13 illustrates an embodiment of a method of virtual reality-based physical therapy.

One embodiment of this bio-feedback tool, shown in FIG. 13, may use the system and a software application for an interactive VR game 1310 that uses the bio-feedback system as an input device to control an avatar 1311 in the game 1310 during upper extremity exercise sessions 1320. For example, the system utilizes the process described in paragraphs 0046-0050 As the user raises his arm, the data generated from this motion is transmitted to the host. Then, the avatar 12 1311 will raise his arm.

In an embodiment, the feedback provided to the patient is a Fugl-Meyer Assessment (FMA). The FMA is a stroke-specific, performance-based impairment index. It is designed to assess motor functioning, balance, sensation and joint functioning in patients with post-stroke hemiplegia. It is applied clinically and in research to determine disease severity, describe motor recovery, and to plan and assess treatment. As the patient completes each level of the game, FMA scores may be computed along with other data analysis such as range of motion, pressure points, or physiological state 1330. The FMA score and other data may provide a therapist with a quantitative assessment of the patient's recovery process.

In another embodiment, the therapist may prescribe a series of exercises for the patient to complete during a therapy session. After each set of exercises is completed, the physical therapist will generate the FMA score and other data analysis 1330 on a host computer.

In another embodiment, the therapist may prescribe a series of exercises for the patient to complete during a therapy session. After each set of exercises is completed, the physical therapist will generate the FMA score and other data analysis 1330 on a host computer.

In another embodiment, the therapist may prescribe a series of exercises for the patient to complete at home. The user will wear the system described herein while performing the prescribed exercises. The data generated may be submitted to the therapist through a secure channel such as an encrypted email or uploaded to a secure web portal or the data may be submitted in person during the patient's next physical therapy session.

Figure 14:
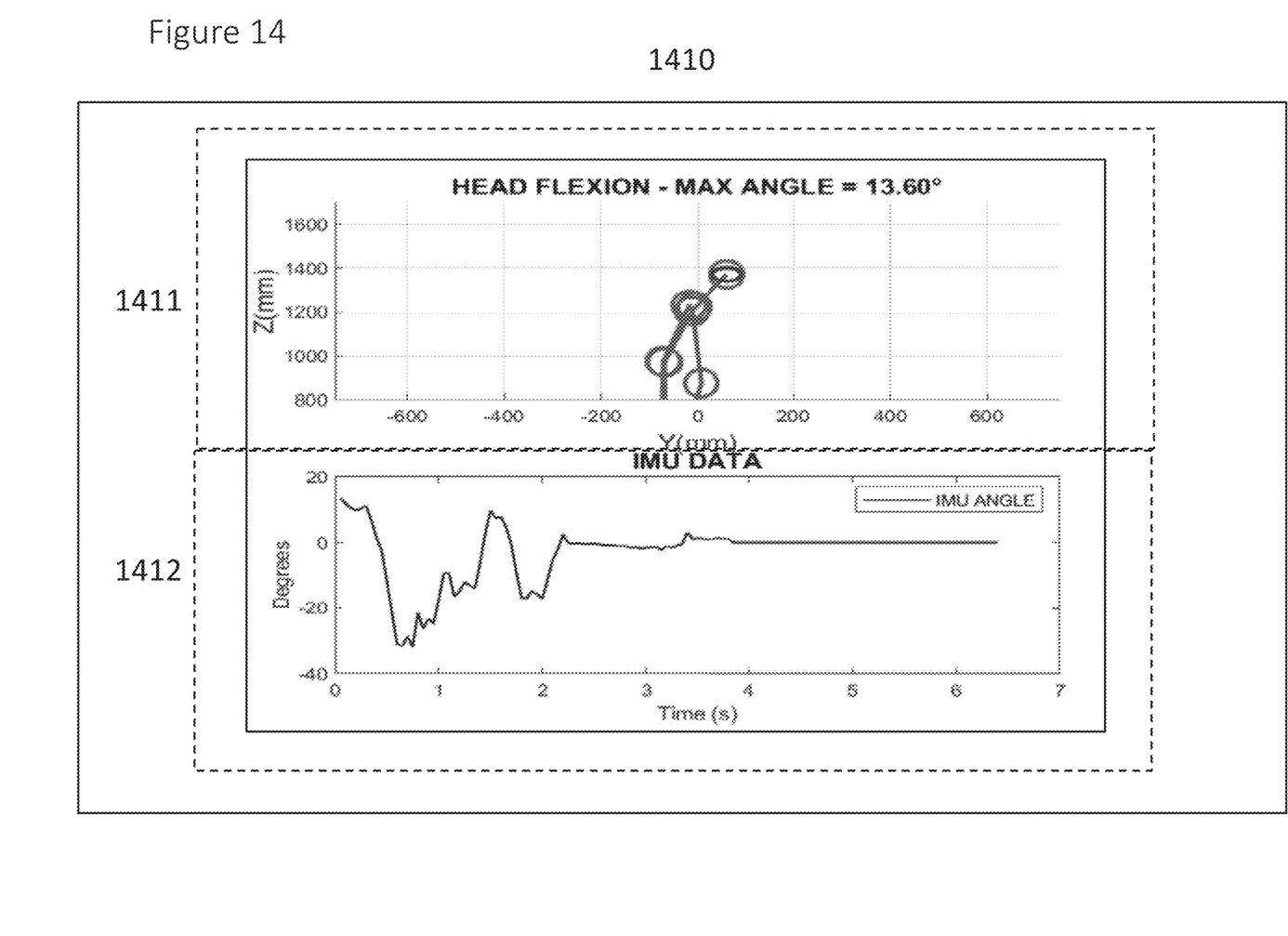
FIG. 14 demonstrates an embodiment of an information display screen of combined nodes data.

FIG. 14 depicts an embodiment of a display screen 1410 during a tracked exercise. A part 1411 of the display 1410 depicts all active nodes. The therapist may desire to display the maximum flexion at the patient's head during an exercise. The therapist may select the point in time where the patient achieved maximum on an IMU graph 1412 to visualize the patient's body position in the node display 1411. The therapist may compare this display 1411 to previous sessions to chart the patient's progress

I claim:

1. A method comprising:
    forming a secure wireless network between a plurality of sensor nodes comprising an electrocardiogram, an electromyogram, and acoustic sensors;
    measuring muscle activation acoustically at each sensor node;
    transmitting muscle activation data from each of the plurality of sensor nodes to a master node;
    compiling the muscle activation data received from each of the plurality of sensor nodes; and
    creating a visual display comparing data from the plurality of sensor nodes captured during a selected span of time,
    wherein the sensor nodes are attached to a wearable garment of clothing at predetermined locations on the garment, and
    wherein the sensor nodes and master node are collectively configured to perform multilateration to locate an external acoustic source.

2. The method of claim 1, further comprising transmitting the data from the plurality of sensor nodes to a host.

3. The method of claim 1, further comprising attaching the master node to the wearable garment of clothing.

4. The method of claim 1, further comprising incorporating the master node into a cell phone application.

5. A wearable biofeedback system comprising:
    an article of clothing to which a plurality of sensor nodes are attached;
    a master node comprising a processor and a wireless antenna, whereby the master node is configured to receive and process data transmitted from all of the sensor nodes;
    the sensor nodes each comprising a plurality of sensors and a wireless antenna;
    the sensors at each sensor node comprising:
        a plurality of microphones, and
        one or more of a gyroscope and an accelerometer,
        wherein one of the plurality of microphones is positioned to face the user's body, and wherein another of the plurality of microphones is positioned to face away from the user's body;
        wherein the wireless antennas are configured to facilitate communication between the master and sensor node(s); and
        wherein the sensor nodes are attached to the article of clothing at predetermined locations on the article of clothing, and
        wherein the sensor nodes, each using its microphone that is positioned to face away from the user's body, are collectively configured to perform multilateration to locate an external acoustic source.

6. The system of claim 5, wherein at least one of the plurality of microphones is configured to capture acoustic data that is provided to the master node, wherein the master node is configured to perform imaging using the acoustic data.

7. The system of claim 5, wherein the article of clothing comprises pockets to attach the sensor nodes adjacent to the user's joints.

8. The system of claim 5, wherein the article of clothing comprises hook and loop fasteners to attach the sensor nodes adjacent to the user's joints.

9. The system of claim 5, wherein the sensors further comprise an electrocardiogram sensor.

10. The system of claim 5, wherein the sensors further comprise an electromyogram sensor.

11. The system of claim 5, wherein the accelerometer and the gyroscope are incorporated together in an inertial management unit.

* * * * *